US009833149B2

(12) United States Patent
Fojtik et al.

(10) Patent No.: US 9,833,149 B2
(45) Date of Patent: Dec. 5, 2017

(54) METHODS, APPARATUS AND SYSTEMS FOR FACILITATING INTRODUCTION OF SHAPED MEDICAL INSTRUMENTS INTO THE BODY OF A SUBJECT (75) Inventors: Shawn P. Fojtik, Park City, UT (US); Leroy D. Jutte, Highlands Ranch, CO (US)

(73) Assignee: CIRCA SCIENTIFIC, LLC, Englewood, CO (US)

( * ) Notice: Subject to any disclaimer, the term of this patent is extended or adjusted under 35 U.S.C. 154(b) by 425 days.

(21) Appl. No.: 13/101,640

(22) Filed: May 5, 2011

(65) Prior Publication Data
US 2012/0010524 A1   Jan. 12, 2012

Related U.S. Application Data (63) Continuation-in-part of application No. 12/406,771, filed on Mar. 18, 2009, now Pat. No. 9,155,476.
(Continued)

(51) Int. Cl.
*A61B 5/01*        (2006.01)
*A61M 25/00*    (2006.01)
(Continued)

(52) U.S. Cl.
CPC .......... *A61B 5/015* (2013.01); *A61B 17/0218* (2013.01); *A61M 25/002* (2013.01);
(Continued)

(58) Field of Classification Search
CPC ....... A61B 5/015; A61B 17/0218; A61B 5/01; A61M 25/002; A61M 25/01
(Continued)

(56) References Cited

U.S. PATENT DOCUMENTS 5,170,803 A   12/1992 Hewson et al.
5,391,155 A *  2/1995 Sachse .................... 604/170.01
(Continued)

FOREIGN PATENT DOCUMENTS

EP      1 504 725 A1    2/2005
JP      HEI 01-107307   7/1989
(Continued)

OTHER PUBLICATIONS

Merriam-Webser's Collegiate Dictionary, 10th ed. Merriam-Webster, Inc. 2001. p. 449.*
(Continued)

*Primary Examiner* — Max Hindenburg
*Assistant Examiner* — Jonathan M Foreman
(74) *Attorney, Agent, or Firm* — Durham Jones & Pinegar, P.C. Intellectual Property Law Group (57) ABSTRACT A method for introducing an elongate medical instrument with a shaped portion into the body of a subject includes at least partially straightening the shaped portion from an exterior of the elongate medical instrument. A retention element may then be introduced into an interior of the shaped portion to maintain the shaped portion in an at least partially straightened configuration as the external force is removed from the shaped portion. With the retention element in place, the shaped portion may be introduced to a desired location within a hollow interior of an internal organ. The retention element may then be removed to enable the shaped portion to return to its desired shape. A straightening apparatus includes the retention element, as well as an external element that at least partially straightens the shaped portion of the elongate medical instrument from the outside. A system includes the elongate medical instrument and the straightening apparatus.

19 Claims, 7 Drawing Sheets

Related U.S. Application Data (60) Provisional application No. 61/037,624, filed on Mar. 18, 2008.

(51) Int. Cl.

| | | |
|---|---|---|
| *A61M 25/01* | (2006.01) | |
| *A61B 17/02* | (2006.01) | |
| *A61B 5/00* | (2006.01) | |
| *A61B 18/00* | (2006.01) | |
| *A61B 17/00* | (2006.01) | |

(52) U.S. Cl.
CPC .............. *A61M 25/01* (2013.01); *A61B 5/01* (2013.01); *A61B 5/6853* (2013.01); *A61B 5/6858* (2013.01); *A61B 5/6859* (2013.01); *A61B 2017/00088* (2013.01); *A61B 2017/00862* (2013.01); *A61B 2018/00797* (2013.01); *A61B 2562/0271* (2013.01)

(58) Field of Classification Search
USPC ..................... 600/433, 434, 585; 604/164.13
See application file for complete search history.

(56) References Cited

U.S. PATENT DOCUMENTS

| | | | |
|---|---|---|---|
| 5,536,274 A * | 7/1996 | Neuss | ............................ 623/1.22 |
| 5,673,695 A | 10/1997 | McGee et al. | |
| 5,803,902 A | 9/1998 | Sienkiewicz et al. | |
| 6,015,382 A | 1/2000 | Zwart et al. | |
| 6,080,118 A | 6/2000 | Blythe | |
| 6,080,160 A | 6/2000 | Chen et al. | |
| 6,106,522 A | 8/2000 | Fleischman et al. | |
| 6,939,313 B2 | 9/2005 | Saadat et al. | |
| 7,140,766 B2 | 11/2006 | Glukhovsky et al. | |
| 7,621,908 B2 | 11/2009 | Miller | |
| 2004/0073132 A1 | 4/2004 | Maahs et al. | |
| 2004/0176699 A1 | 9/2004 | Walker et al. | |
| 2005/0240116 A1 | 10/2005 | Saadat et al. | |
| 2006/0085054 A1 | 4/2006 | Zikorus et al. | |
| 2006/0106375 A1 | 5/2006 | Werneth et al. | |
| 2007/0066968 A1 | 3/2007 | Rahn | |
| 2007/0179378 A1 | 8/2007 | Boese et al. | |
| 2007/0225701 A1 | 9/2007 | O'Sullivan | |
| 2008/0033415 A1 | 2/2008 | Rieker et al. | |
| 2008/0077126 A1 | 3/2008 | Rashidi | |
| 2008/0177175 A1 | 7/2008 | Mottola et al. | |
| 2008/0215047 A1 | 9/2008 | Calabro et al. | |
| 2008/0243112 A1 | 10/2008 | De Neve | |
| 2010/0030098 A1 | 2/2010 | Fojtik | |
| 2010/0312223 A1 * | 12/2010 | Kozak et al. | .................. 604/528 |

FOREIGN PATENT DOCUMENTS

| | | |
|---|---|---|
| JP | HEI 03-056048 A2 | 8/1991 |
| JP | 2002-541905 A | 12/2002 |
| JP | 2005-095602 A | 4/2005 |
| JP | 2007-537784 A | 12/2007 |
| WO | 00/62699 A2 | 10/2000 |
| WO | 02/43789 A2 | 6/2002 |
| WO | 2005/117755 A2 | 12/2005 |
| WO | 2006/055286 A2 | 5/2006 |
| WO | 2007/001981 A2 | 1/2007 |

OTHER PUBLICATIONS

International Searching Authority, U.S., "International Search Report and Written Opinion" in related PCT application No. PCT/US2012/036814.

Korean Intellectual Property Office as International Searching Authority "International Search Report and Written Opinion" dated Nov. 2, 2009, in related PCT application No. PCT/US2009/037571.

European Patent Office, "Supplementary European Search Report," in related European Application No. 09721913.3, dated May 8, 2013.

International Searching Authority, U.S., "International Search Report and Written Opinion" in related PCT application No. PCT/US2011/036330, dated Aug. 16, 2011.

* cited by examiner

METHODS, APPARATUS AND SYSTEMS FOR FACILITATING INTRODUCTION OF SHAPED MEDICAL INSTRUMENTS INTO THE BODY OF A SUBJECT

CROSS-REFERENCE TO RELATED APPLICATIONS

This application is a continuation-in-part of U.S. patent application Ser. No. 12/406,771, filed Mar. 18, 2009, in which a priority claim has been made pursuant to 35 U.S.C. §119(e) to U.S. Provisional Patent Application 61/037,624, filed Mar. 18, 2008.

TECHNICAL FIELD

The present invention relates generally to methods, apparatus and systems for introducing shaped medical instruments, such as catheters, into the body of a subject. More specifically, the present invention relates to methods, apparatus and systems for at least partially straightening or even substantially straightening shaped sections of medical instruments to facilitate their introduction into the body of a subject. Further, the present invention includes methods, apparatus and systems for facilitating the introduction of medical instruments into hollow organs to maximize or optimize contact with the interior surfaces of hollow organs or to change the shapes of (e.g., flatten, etc.) or otherwise manipulate the hollow organs.

SUMMARY

The present invention includes embodiments of methods, apparatus and systems that facilitate the introduction of shaped medical instruments into the body of a subject. Without limiting the scope of the present invention, methods and apparatus that incorporate teachings of the present invention are useful with a variety of different elongate medical instruments, including, but not limited to, esophageal temperature sensing catheters of the types disclosed by U.S. Provisional Patent Application No. 61/037,624, filed Mar. 18, 2008 (the "'624 Provisional Application"), and U.S. patent application Ser. No. 12/406,771, filed Mar. 18, 2009 (the "'771 Application"), the entire disclosures of both of which are, by this reference, hereby incorporated herein. Some embodiments of systems of the present invention may include elongate medical instruments of the types disclosed by the '624 Provisional Application and the '771 Application.

A method of the present invention may include applying external force to at least a shaped portion of a hollow, shaped elongate medical instrument (e.g., a catheter with a shaped portion, such as a serpentine portion of an esophageal temperature sensing catheter, etc.) to at least partially straighten, or even substantially straighten, the same. With the shaped portion of the elongate medical instrument at least partially straightened, a relatively rigid (when compared with the medical instrument), substantially linear or curvilinear internal element (e.g., a wire, etc.), or "retention element," may be introduced into an interior (e.g., a lumen, etc.) of the elongate medical instrument.

With the internal element in place, the external force may be removed. As the external force is removed, the internal element withstands or resists deformation under forces applied by the shaped portion of the elongate medical instrument and retains a somewhat linear configuration and/or applies force internally to at least the shaped portion, substantially retaining the shaped portion in the at least partially straightened configuration. While the configuration of the shaped portion may change somewhat as the external force is removed, the ability of the internal element to retain the shaped portion in a partially straightened configuration is considered, for purposes of this disclosure, to comprise substantial retention of the shaped portion in the at least partially straightened configuration.

The at least partially straightened configuration of the shaped portion of the elongate medical instrument facilitates its introduction into the body of a subject. In some embodiments, depending at least in part upon the relaxed shape of the shaped portion of the elongate medical instrument, at least partially straightening the shaped portion may reduce its effective width (i.e., the distance from one lateral extent of the entire shaped portion to the opposite lateral extent of the shaped portion), may minimize contact between the shaped portion and internal surfaces of any hollow organ into and/or through which the elongate medical instrument is introduced and/or may prevent the shaped portion from engaging, or grabbing onto, any part of any hollow organ into and/or through which the shaped portion is introduced.

Once the shaped portion of the elongate medical instrument has been positioned at an intended location within the interior of the hollow organ, the internal element may be removed from at least the interior of shaped portion of the elongate medical instrument. Removal of the internal element removes the internal force that holds the shaped portion in the at least partially straightened configuration, enabling the shaped portion to return to its relaxed, shaped configuration. As the shaped portion of the elongate medical instrument returns to its relaxed, shaped configuration, its contact with an interior surface of the hollow organ may increase or it may manipulate the shape of (e.g., flatten, etc.) the hollow organ.

In another aspect, the present invention includes straightening apparatus. A straightening apparatus of the present invention may least partially straighten a shaped portion of an elongate medical instrument. In some embodiments, such an apparatus includes an external element and a separate internal element.

The external element of a straightening apparatus may comprise a hollow elongate element with a length that will at least partially straighten a shaped portion of an elongate medical instrument (e.g., a curved portion of a medical instrument, such as the serpentine portions of various esophageal temperature sensing catheters disclosed in the '624 Provisional Application and the '771 Application, etc.). A passage through the external element may be configured to receive the elongate medical instrument. As the external element is translated (e.g., moved, slid, etc.) along the length of the elongate medical instrument and over the shaped portion, a wall of the external element exerts an external force against the shaped portion, causing it to at least partially straighten.

The internal element of the straightening apparatus, which is also referred to herein as a "retention element," may comprise an elongate element that is configured to fit within an interior (e.g., a lumen, etc.) of the elongate medical instrument and, thus, to be introduced into and at least temporarily reside within the interior of the elongate medical instrument. The internal element of the straightening apparatus may be relatively rigid when compared with the shaped portion of the elongate medical instrument. The relative rigidity of the internal element may enable the internal element to withstand force applied by the shaped portion of the elongate medical instrument, or to exert force against the shaped portion of the elongate medical instrument from within, which may hold the shaped portion in a partially straightened configuration while the internal element resides within the interior of the elongate medical instrument.

According to another aspect, the present invention includes a system for introducing an elongate medical instrument into the body of a subject. Such a system includes straightening apparatus, which may include an external element and an internal element, such as those described above, as well as an elongate medical instrument with which the external element and the internal element are configured to be used.

Other aspects, as well as features and advantages of various aspects, of the present invention will become apparent those of skill in the art through consideration of the ensuing description, the accompanying drawings and the appended claims.

DETAILED DESCRIPTION

Figure 1:
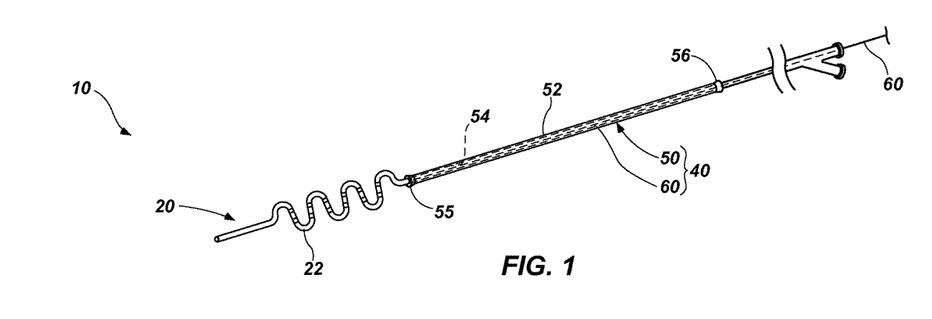
FIG. 1 depicts an embodiment of a straightening apparatus of the present invention, as well as a system that includes a straightening apparatus and an embodiment of an elongate medical instrument, with a shaped portion of the elongate medical instrument in a relaxed, or "pre-deployment," configuration.
Figure 2:
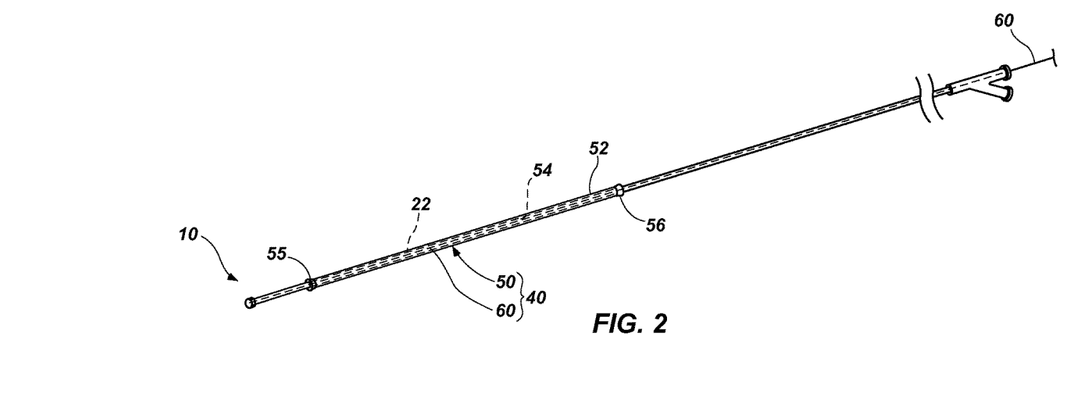
FIG. 2 illustrates the embodiment of straightening apparatus and system shown in FIG. 1, with the shaped portion of the elongate medical instrument in an at least partially straightened, or "deployment," configuration.

With reference to FIGS. 1 and 2, an embodiment of a system 10 for introducing an elongate medical instrument into a hollow organ of the body of a subject is illustrated. The system 10 shown in FIGS. 1 and 2 includes the medical instrument 20 and a straightening apparatus 40. In the depicted embodiment, the straightening apparatus 40 includes an external element 50 and an internal element 60.

Figure 3:
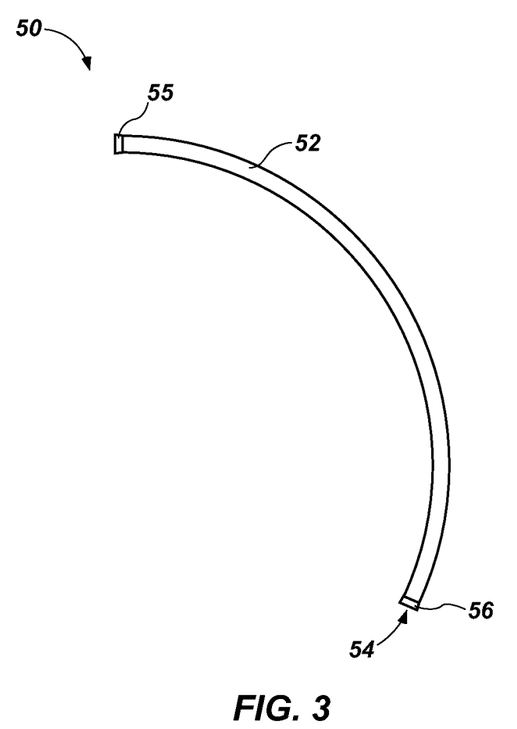
FIG. 3 depicts an embodiment of an external element of straightening apparatus.

With continued reference to FIGS. 1 and 2, and with added reference to FIG. 3, various features of an external element 50 of a straightening apparatus 40 (FIGS. 1 and 2) are described. In some embodiments, the external element 50 may be linear or substantially linear, while in other embodiments, it may have a curvilinear configuration.

The external element 50 may comprise an elongate element with an internal passage 54 defined by at least one outer wall 52. The passage 54 has dimensions large enough to enable it to receive a shaped portion 22 (FIGS. 1 and 2) of an elongate medical instrument 20 (FIGS. 1 and 2) and small enough to cause it to engage the shaped portion 22 to an extent sufficient to partially straighten or even substantially straighten the shaped portion 22 of the elongate medical instrument 20. The configuration of at least one outer wall 52 of the external element 50 and/or the material from which the at least one outer wall 52 is formed enable the at least one outer wall 52 to exert sufficient resistance against the shaped portion 22 to partially or substantially straighten the shaped portion 22 while the shaped portion 22 is positioned within the passage 54 and constrained by the outer wall 52 of the external element 50.

While the outer wall 52 of the exterior element 50 has a configuration and/or is formed from a material (e.g., polypropylene, etc.) that will enable it to partially or substantially straighten the shaped portion 22 of the medical instrument 20 (FIGS. 1 and 2), the exterior element 50 may be flexible enough to enable it, and any elongate medical instrument 20 and other components with which it is assembled, to be stored and/or transported in a coiled or otherwise compacted configuration. To illustrate this optional characteristic, the external element 50 is shown in FIG. 3 as having a curvilinear configuration.

Although FIGS. 1-3 show the external element 50 has comprising a complete tube, other configurations of external elements are also within the scope of the present invention. In addition, external elements with incomplete configurations (e.g., configurations in which the outer wall 52 does not completely encompass the length of the passage 54, etc.) are within the scope of the present invention.

In some embodiments, the passage 54 of an external element 50 of a straightening apparatus 40 (FIGS. 1 and 2) of the present invention may include enlarged ends 55, 56. The enlarged ends 55 and 56 may be tapered to facilitate the introduction of an end (not shown) of a medical instrument 20 (FIGS. 1 and 2) therein.

Figure 4:
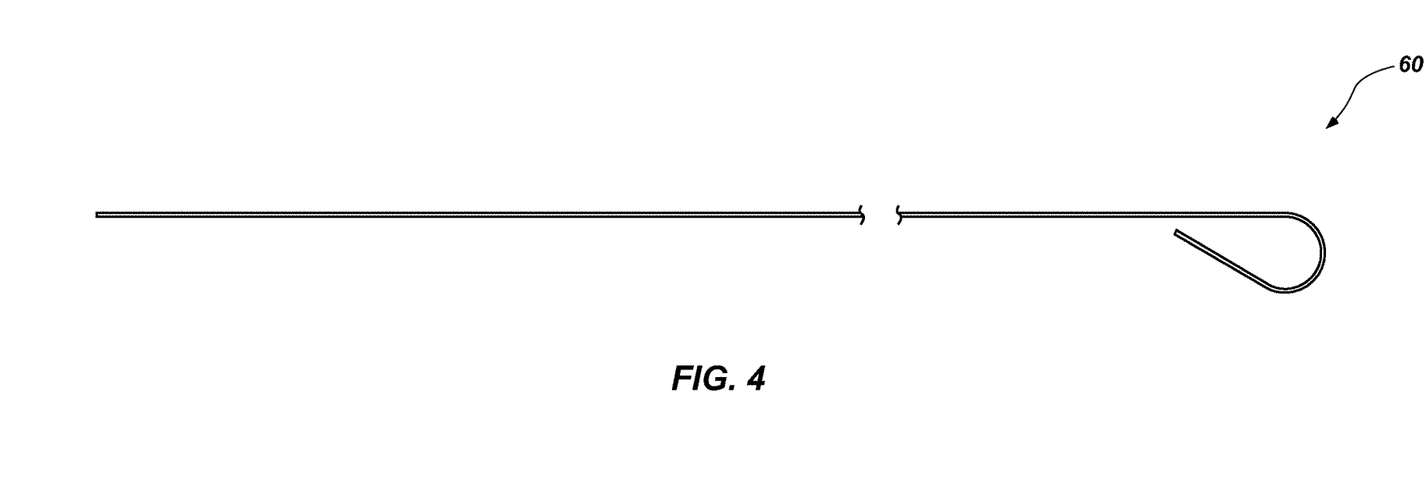
FIG. 4 depicts an embodiment of an internal element of straightening apparatus.

Turning now to FIG. 4, while maintaining reference to FIGS. 1 and 2, an internal element 60, or "retention element," of a straightening apparatus 40 of the present invention may include an elongate element that may be introduced into and reside within an interior (e.g., a lumen, etc.) of the medical instrument 20 (FIGS. 1 and 2), including its shaped portion 22. One or both of the configuration of the internal element 60 and/or the materials from which the internal element 60 is formed (e.g., stainless steel, etc.) impart it with sufficient rigidity to resist bending when disposed within the interior of the shaped portion 22 and, thus, to retain the shaped portion 22 in an at least partially straightened or substantially straightened configuration.

In the embodiment illustrated by FIG. 4, the internal element 60 comprises a wire, or stylet. In various embodiments, an internal element 60 that comprises a wire, or stylet, may include a single filament, a coiled filament surrounding a linear or substantially linear (e.g., curvilinear, etc.) core, a plurality of twisted or woven filaments or any other suitable configuration. In particular, the illustrated embodiment of internal element 60 comprises a single filament wire with a 0.023 inch diameter.

Figure 5:
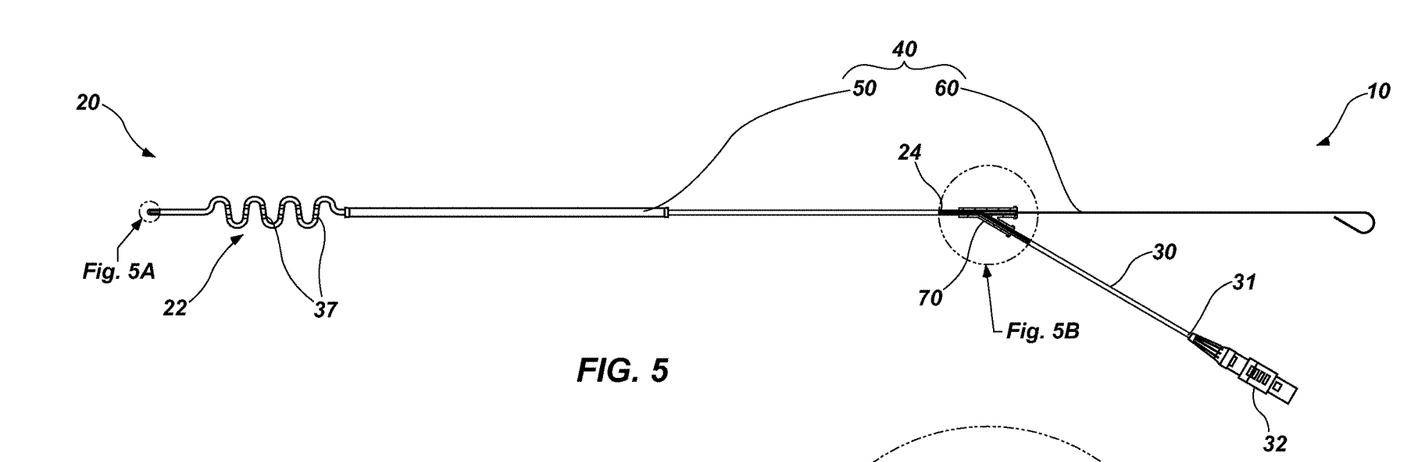
FIGS. 5, 5A and 5B depict the system shown in FIGS. 1 and 2, as well as other components that may be included in a system that incorporates teachings of the present invention.
Figure 5A:
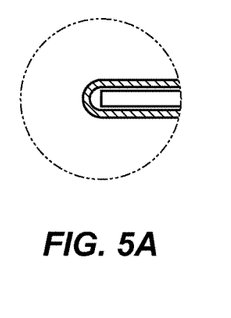
Figure 5B:
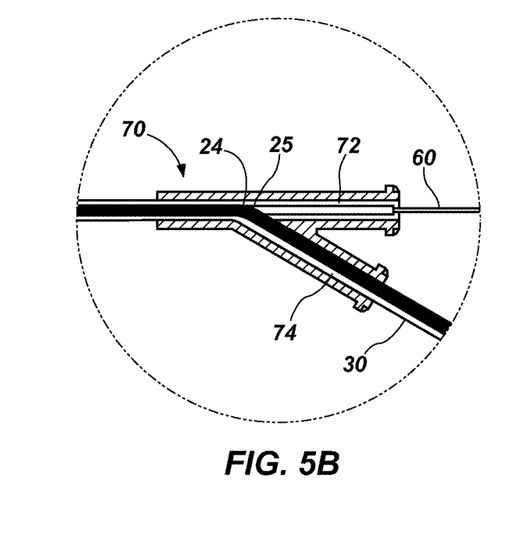

Turning now to FIGS. 5 through 5B, an additional, optional feature of a system 10 that incorporates teachings of the present invention is depicted. Specifically, the embodiment of system 10 shown in FIGS. 5 and 5B includes a branched connector 70 (e.g., a Y-connector, a T-connector, etc.), which is configured to be positioned at or adjacent to a proximal end 24 of the medical instrument 20. A branched connector 70 may include a plurality of ports 72, 74 that are configured to communicate with a lumen 25 and/or other features of the medical instrument 70. As illustrated, one port 72 of the branched connector 70 may be configured to receive a portion of the internal element 60 of the straightening apparatus 40, while another port 74 of the branched connector 70 may be configured to enable control over another functionality of the elongate medical instrument 20. In embodiments where the elongate medical instrument comprises an esophageal temperature sensing catheter or other temperature sensing device, the other port 74 may be configured to receive a thermistor cable 30 that extends into the elongate medical instrument 20.

Figure 6:
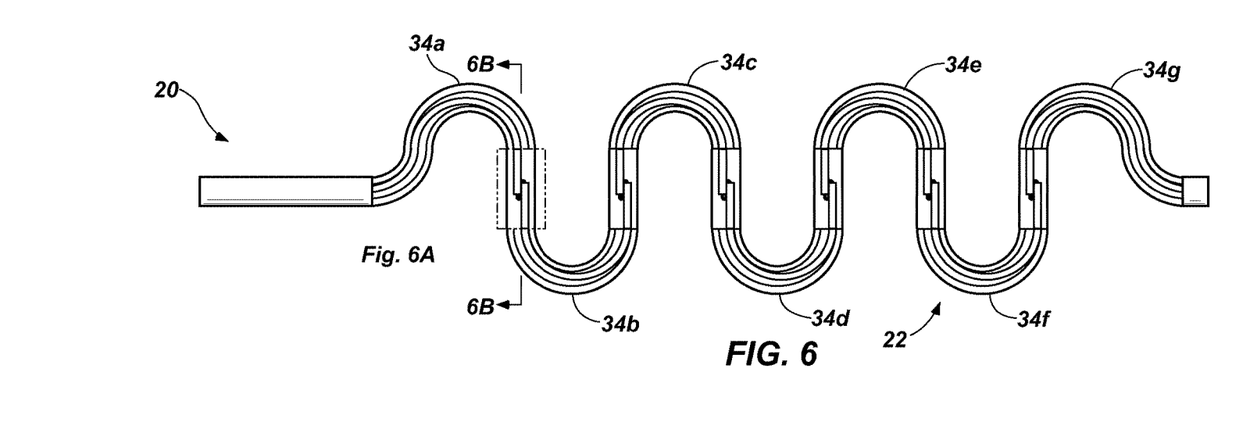
FIGS. 6, 6A, 6B and 6C illustrate a specific embodiment of elongate medical instrument with which a method and/or straightening apparatus (see, e.g., the embodiments of internal element and external element shown in FIGS. 3 and 4, respectively) of the present invention may be used.
Figure 6A:
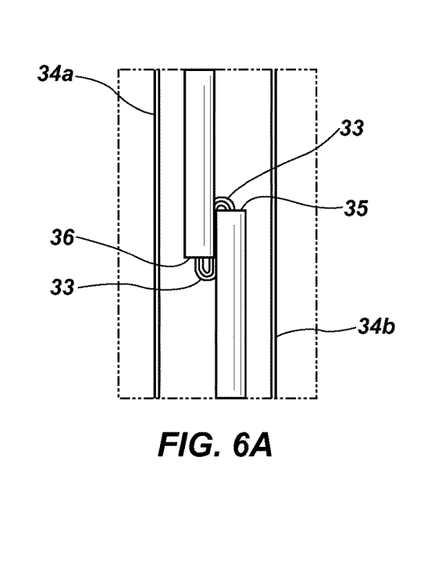
Figure 6B:
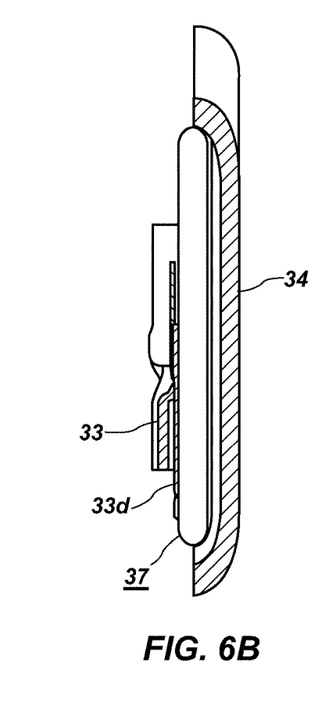
Figure 6C:
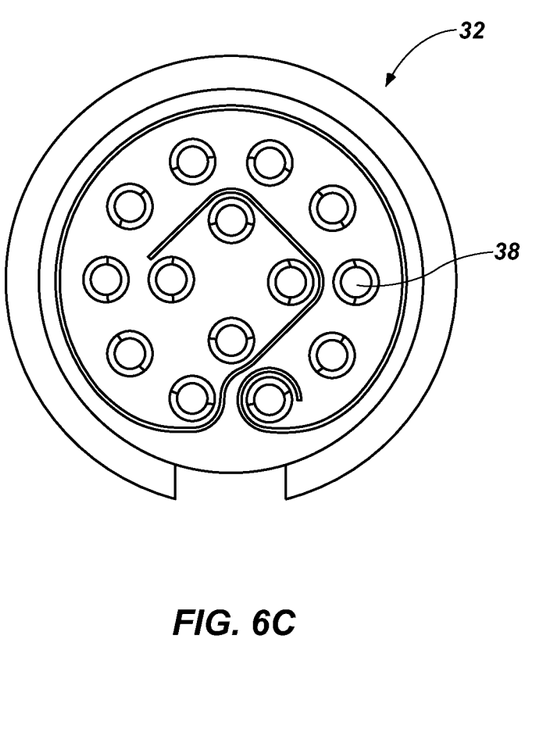

FIG. 5 also depicts the elongate medical instrument 20 as including an embodiment of a connector 32 at a proximal end 31 of the thermistor cable 30. Other features of a specific embodiment of medical instrument 20 are shown in FIGS. 6 through 6C. Specifically, FIGS. 6 through 6C show an example of a configuration for a thermistor cable 30. The depicted embodiment of thermistor cable 30 includes at least thirteen (13) electrically isolated filaments, or wires 33. In addition, the depicted thermistor cable 30 includes seven (7) segments 34 (34a, 34b, 34c, etc.), with the ends 35, 36 of adjacent segments 34 overlapping each other. The number of wires 33 and the number of segments 34 is at least partially dependent upon the desired number of thermistor contacts or bands, or more simply "thermistors" 37 (FIG. 5), for a particular medical instrument 20 (e.g., there are twelve (12) thermistor contacts 37 in the depicted embodiment, etc.). In the depicted embodiment, one of the thirteen wires 33 is a common wire that communicates with each of the thermistors 37, while each of the other wires 33 communicates with a single thermistor 37, or is a "thermistor-specific" wire. At each overlap location, at least some of the wires 33 emerge from the end 36 of one segment 34 (e.g., segment 34a, etc.) and extend into the adjacent end 35 of the next segment 34 (e.g., segment 34b, etc.). As shown in FIG. 6B, at that overlap location, a distal end 33d of one thermistor-specific wire 33 and a looped portion of the common wire 33 extend back toward the segment 34 (e.g., segment 34a, etc.) from which it emerged, while another thermistor-specific wire 33 and another looped portion of the common wire 33 extend in the opposite direction, toward or along the next segment (e.g., segment 34b, etc.). The distal end 33d of each thermistor-specific wire 33 and an exposed region of the looped portion of the common wire 33 that corresponds to each thermistor-specific wire 33 are electrically coupled to a corresponding thermistor 37 (FIG. 5), which is exposed to an exterior surface of the shaped portion 22 of the elongate medical instrument 20.

FIG. 6C depicts an embodiment of a connector 32 and pin 38 layout that may be used with a thermistor cable 30 (FIGS. 5 and 5B) of the embodiment of medical instrument 20 depicted by FIGS. 6 through 6B. The connector 32 is located at the proximal end of the thermistor cable 30, with each pin 38 being electrically coupled to the proximal end (not shown) of each wire 33 of the thermistor cable 30.

In some embodiments, the elongate medical instrument 20 may be at least partially radio-opaque. At least the shaped portion 22 of an at least partially radio-opaque elongate medical instrument 20 may be formed from a radio-opaque material, or it may include one or more radio-opaque features.

Figure 7A:
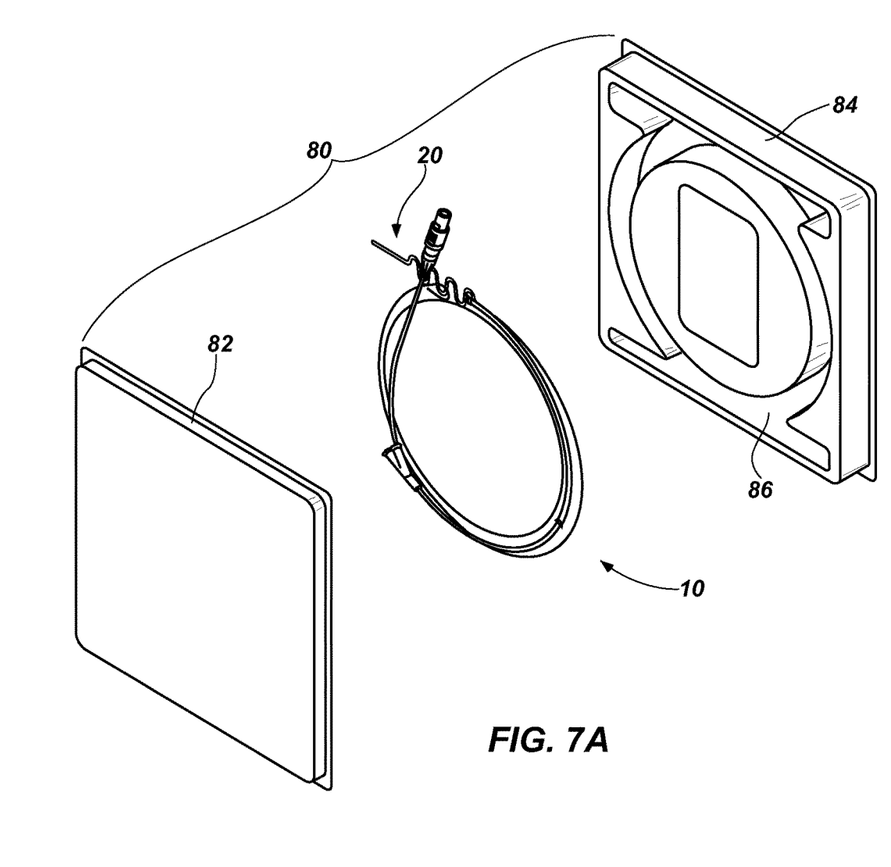
FIGS. 7A and 7B show an embodiment of a packaged system of the present invention.
Figure 7B:
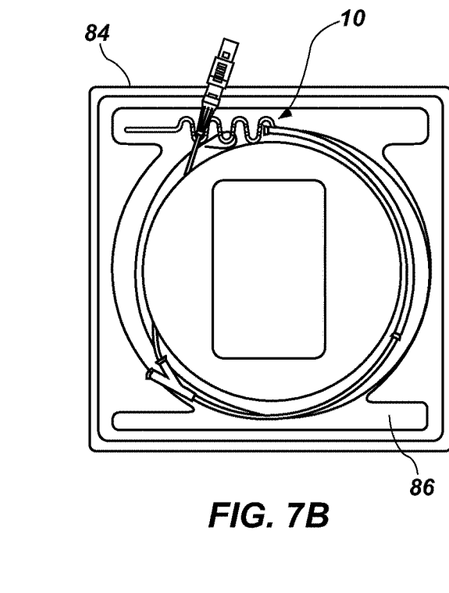

In FIGS. 7A and 7B, an embodiment of a package 80 is shown. The illustrated embodiment of package 80 includes a base 84 and a cover 82. As shown, the base 84 may include a receptacle 86 for receiving a system 10 (see, e.g., FIG. 5) that incorporates teachings of the present invention. More specifically, the receptacle 86 may be configured to receive the system with the elongate medical instrument 20 thereof in a compact configuration, such as the depicted coil. The cover 82 may be configured for assembly with the base 84 and, thus, to at least partially retain a system 10 within the receptacle 86 of the base 84.

In the depicted embodiment, the base 84 and cover 82 of the package comprise molded elements. Of course, other embodiments of packages are also within the scope of the present invention.

When use of an elongate medical instrument 20 with a shaped portion 22 is desired, a system 10 that includes the elongate medical instrument 20 may be removed from its package 80. The system 10 may be visually inspected for damage, kinks, debris and missing components. In some embodiments, functionality of the elongate medical instrument 20 may be tested before its introduction into the body of a subject. Use of the system 10 may be continued if no defects are observed.

With the system 10 in hand, an external force may be applied to at least the shaped portion 22 of the elongate medical instrument 20. In some embodiments, this act may be accomplished with an external element 50 of a straightening apparatus 40, which may be pre-assembled with the elongate medical instrument 20, as shown in FIG. 1. The external element 50 may be positioned (e.g., moved distally along the elongate medical instrument shown in FIG. 1, etc.) over at least a portion of the shaped portion 22 of the elongate medical instrument 20, as depicted by FIG. 2.

With the shaped portion 22 of the elongate medical instrument 20 at least partially straightened, a relatively rigid (when compared with the elongate medical instrument), substantially linear or curvilinear internal element 60 may be introduced into at least part of the interior of the shaped portion 22. FIG. 2 illustrates an embodiment of such an internal element 60. The internal element 60 may also come preassembled with the elongate medical instrument 20, as depicted by FIGS. 7A and 7B. In the illustrated embodiment, the act of introducing the internal element 60 at least partially into the shaped portion 22 of the elongate medical instrument 20 may be effected by grasping a proximal end of the internal element 60 and moving the internal element 60 distally into the interior of the shaped portion 22. In some embodiments, the distance the internal element 60 is moved may be limited by a feature at or near a proximal end of the internal element 60.

With the internal element in place within at least part of the shaped portion 22, the external force (e.g., that applied by the external element 50, etc.) may be removed. As the external force is removed, the internal element 60 withstands or resists the tendency of the shaped portion 22 to return to its relaxed, shaped configuration and, therefore, retains the shaped portion 22 the at least partially straightened or substantially straightened configuration.

The at least partially straightened configuration or substantially straightened configuration of the shaped portion 22 of the elongate medical instrument 20 facilitates its introduction into the body of a subject. In some embodiments, depending at least in part up on the relaxed shape of the shaped portion 22 of the elongate medical instrument 20, at least partially straightening a shaped portion of the elongate medical instrument 20 may reduce the effective width of the shaped portion 22, may minimize contact between the shaped portion 22 and internal surfaces of any organ into and/or through which the elongate medical instrument 20 is introduced and/or may prevent the shaped portion 22 of the elongate medical instrument 20 from engaging, or grabbing onto, any part of any organ into and/or through which the elongate medical instrument 20 is introduced.

Before introducing the elongate medical instrument 20 into the body of a subject, a lubricant (e.g., a water soluble material, etc.) may be applied to at least the shaped portion 22. Introduction of the shaped portion 22 of the elongate medical instrument 20 into the interior of a hollow organ may be effected with visual guidance; for example, under fluoroscopic x-ray. The use of visual guidance may prevent damage to a subject's body during introduction of the shaped portion into the hollow organ.

Once the shaped portion 20 of the elongate medical instrument 20 has been positioned at an intended location within the interior of the hollow organ, the internal element 60 may be removed from the interior of the shaped portion 22 and, optionally, from the interior of the entire elongate medical instrument 20. Removal of the internal element 60 removes the internal force that holds the shaped portion 22 in the at least partially straightened or substantially straightened configuration, enabling the shaped portion 22 to return to its relaxed, shaped configuration, such as that depicted by FIG. 1. As the shaped portion 22 of the elongate medical instrument 20 returns to its relaxed, shaped configuration, it may manipulate the shape of (e.g., flatten, etc.) the hollow organ. The position of the shaped portion 22 within the interior of the hollow organ may be viewed under fluoroscopic x-ray and, if necessary, changed.

In embodiments where operation of the elongate medical instrument 20 requires assembly of the elongate medical instrument 20 with an exterior apparatus, such assembly may be effected. Without limiting the scope of the present invention, when the elongate medical instrument 20 comprises a temperature sensing device, such as an esophageal temperature sensing catheter, thermistors or other temperature sensing elements of the elongate medical instrument may be electrically coupled to an appropriate sensor.

Once use of the elongate medical instrument 20 is complete, it may be disconnected from any exterior apparatus. Depending upon the type of elongate medical instrument 20 used, it may be discarded or cleaned and sterilized for subsequent use.

Although the foregoing description contains many specifics, these should not be construed as limiting the scope of the invention or of any of the appended claims, but merely as providing information pertinent to some specific embodiments that may fall within the scopes of the invention and the appended claims. Other embodiments of the invention may also be devised which lie within the scopes of the invention and the appended claims. Features from different embodiments may be employed in combination. The scope of the invention is indicated and limited only by the appended claims and their legal equivalents. All additions, deletions and modifications to the invention, as disclosed herein, that fall within the meaning and scopes of the claims are to be embraced thereby.

What is claimed:

1. An apparatus for straightening a shaped portion of an elongate medical instrument, comprising:
    an external element:
        configured to receive an elongate medical instrument;
        having a length configured for storage over a substantially linear portion of the elongate medical instrument at a location between a proximal end of the elongate medical instrument and a shaped portion of the elongate medical instrument continuous with the substantially linear portion while the shaped portion of the elongate medical instrument is introduced into and resides within a hollow organ of a subject;
        configured to be selectively positioned over the shaped portion of the elongate medical instrument to force the shaped portion into an at least partially straightened configuration prior to introduction of the shaped portion into the hollow organ of the subject; and
        configured to be removed from the shaped portion of the elongate medical instrument before the shaped portion of the elongate medical instrument is introduced into the hollow organ of the subject; and
    an internal element including an elongate element for retaining the shaped portion of the elongate medical instrument in the at least partially straightened configuration:
        following removal of the external element from the elongate medical instrument; and
        while the shaped portion of the elongate medical instrument is introduced into the hollow organ of the subject without the external element residing thereon.

2. The apparatus of claim 1, wherein the external element comprises an elongate element with a wall defining a passage therethrough, the passage being configured to receive at least a portion of the shaped portion of the elongate medical instrument, the wall being configured to force the shaped portion into the at least partially straightened configuration.

3. The apparatus of claim 2, wherein the external element is substantially linear.

4. The apparatus of claim 2, wherein the external element is curvilinear.

5. The apparatus of claim 1, wherein the internal element comprises a wire.

6. The apparatus of claim 5, wherein a rigidity of the wire exceeds a rigidity of at least the shaped portion of the elongate medical instrument.

7. The apparatus of claim 1, wherein the internal element is configured to be introduced into the shaped portion of the elongate medical instrument only when the shaped portion is in the at least partially straightened configuration.

8. An apparatus for straightening a serpentine portion of an elongate medical instrument, comprising:
    an external element:
        with a lumen extending through a length thereof for receiving a portion of a length of an elongate medical instrument, including a serpentine portion of the elongate medical instrument located intermediately along the length of the elongate medical instrument;
        including a large, tapered opening at an end of the lumen to facilitate introduction of the external element onto the serpentine portion of the elongate medical instrument;
        having a length for selective positioning over:
            an entirety of the serpentine portion of the elongate medical instrument; and
            solely on a substantially linear portion of the elongate medical instrument between the serpentine portion and a proximal end of the elongate medical instrument;
        configured to force the serpentine portion of the elongate medical instrument into an at least partially straightened configuration; and
        configured for removal from the serpentine portion of the elongate medical instrument before the serpentine portion of the elongate medical instrument is introduced into a body of a subject; and
    an internal element configured to:

be positioned within a lumen extending through the elongate medical instrument, including the serpentine portion of the elongate medical instrument while the serpentine portion is in the at least partially straightened configuration; and hold the serpentine portion of the elongate medical instrument in the at least partially straightened configuration:
following removal of the external element from the elongate medical instrument; and
while the serpentine portion of the elongate medical instrument, without the external element thereon, is introduced into the body of the subject.

9. The apparatus of claim 8, wherein the external element and the internal element are configured for use with a temperature sensing catheter.

10. The apparatus of 8, wherein an end of the external element is fluted to facilitate introduction of the serpentine portion of the elongate medical instrument into the lumen of the external element.

11. The apparatus of claim 8, wherein the external element is curvilinear.

12. The apparatus of claim 11, wherein the external element is flexible.

13. The apparatus of claim 8, wherein the internal element is substantially linear.

14. The apparatus of claim 8, wherein a rigidity of the internal element exceeds a rigidity of at least the shaped portion of the elongate medical instrument.

15. An apparatus for straightening a shaped portion of an elongate medical instrument, comprising:
an external element:
including a lumen extending through a length thereof for receiving a shaped portion of an elongate medical instrument located along a length of the elongate medical instrument and a taper at an end of the lumen to facilitate introduction of the external element over the shaped portion of the elongate medical instrument;
configured to force the shaped portion of the elongate medical instrument into an at least partially straightened configuration; and
configured to be removed from the shaped portion of the elongate medical instrument before insertion of the elongate medical instrument into a body of a subject; and
an internal element:
comprising an elongate element having sufficient flexibility to follow a curvilinear path but having sufficient rigidity to resist conformation to a shape of the shaped portion of the elongate medical instrument;
configured to be positioned within a lumen extending through the elongate medical instrument, including the shaped portion of the elongate medical instrument while the shaped portion is in the at least partially straightened configuration, but not while the shaped portion is in a relaxed configuration; and
configured to hold the shaped portion of the elongate medical instrument in the at least partially straightened configuration:
following removal of the shaped portion of the elongate medical instrument from the external element; and
after the external element has been removed from the shaped portion of the elongate medical instrument, while the shaped portion of the elongate medical instrument is introduced into the body of the subject.

16. The apparatus of 15, wherein an end of the external element is fluted to facilitate introduction of the shaped portion of the elongate medical instrument into the lumen of the external element.

17. The apparatus of claim 15, wherein the external element is substantially curvilinear.

18. The apparatus of claim 17, wherein the external element is flexible.

19. The apparatus of claim 15, wherein the external element: has a length sufficient to reside over an entirety of the shaped portion of elongate medical instrument in the at least partially straightened configuration but short enough to be stored on a substantially linear portion of the elongate medical instrument between the shaped portion and a proximal end of the elongate medical instrument.

* * * * *